United States Patent
Katayama et al.

(10) Patent No.: US 7,256,001 B2
(45) Date of Patent: Aug. 14, 2007

(54) REAGENT FOR DETERMINING LAMININ 5 ANTIGEN IN BIOLOGICAL SAMPLE AND ASSAY METHOD

(75) Inventors: Masahiko Katayama, Tukuba (JP); Noriko Sanzen, Nagakute-machi (JP); Kiyotoshi Sekiguchi, Suita (JP)

(73) Assignee: Eisai R&D Management Co., Ltd., Bunkyo-ku, Tokyo (JP)

( * ) Notice: Subject to any disclaimer, the term of this patent is extended or adjusted under 35 U.S.C. 154(b) by 480 days.

(21) Appl. No.: 10/487,321

(22) PCT Filed: Aug. 19, 2002

(86) PCT No.: PCT/JP02/08347

§ 371 (c)(1),
(2), (4) Date: Feb. 17, 2004

(87) PCT Pub. No.: WO03/016907

PCT Pub. Date: Feb. 27, 2003

(65) Prior Publication Data

US 2004/0265937 A1     Dec. 30, 2004

(30) Foreign Application Priority Data

Aug. 17, 2001  (JP)  ............... 2001-247685
Feb. 7, 2002   (JP)  ............... 2002-031181
Apr. 9, 2002   (JP)  ............... 2002-106468

(51) Int. Cl.
    G01N 33/53     (2006.01)
(52) U.S. Cl. ....................................... 435/7.1
(58) Field of Classification Search ................ 435/7.1
    See application file for complete search history.

(56) References Cited

U.S. PATENT DOCUMENTS 5,445,948 A * 8/1995 Shimizu et al. ............ 435/69.7
6,143,505 A   11/2000 Tryggvason et al. ......... 435/7.1

FOREIGN PATENT DOCUMENTS

JP        2001-172196       6/2001

OTHER PUBLICATIONS

Koshikawa, et al., "Overexpression of Laminin γ2 Chain Monomer in Invading Gastric Carcinoma Cells" *Cancer Research*, 59: 5596-5601, 1999.

Manda, et al., "Differential Expression of the LAMB3 and LAMC2 Genes Between Small Cell and Non-Small Cell Lung Carcinomas", *Biochemical and Biophysical Research Communications*, 275: 440-445, 2000.

Palacios, et al., "The Short Arm of the Laminin γ2 Chain Plays a Pivotal Role in the Incorporation of Laminin 5 into the Extracellular Matrix and in Cell Adhesion", *The Journal of Cell Biology*, 153(4): 835-849, 2001.

Sasaki, et al., "short Arm Region of Laminin-5 γ2 Chain: Structure, Mechanism of Processing and Binding to Heparin and Proteins", *Journal of Molecular Biology*, 314: 751-763, 2001.

Alnabbas, et al., "Elevated Laminin Concentrations in Lung Secretions of Preterm Infants Supported by Mechanical Ventilation are Correlated with Radiographic Abnormalities", *The Journal of Pediatrics*, 131(4): 555-560, 1997.

Kropf, et al., "The Prognostic Value of Extracellular Matrix Component Concentrations in Serum During Treatment of Adult Respiratory Distress Syndrome with Extracorporeal $CO_2$ Removal", *Eur. J. Clin. Chem. Clin. Biochem.*, 29: 805-812, 1991.

Nebot, et al., "Laminin 5 in the Human Thymus: Control of T Cell Proliferation via $\alpha_6\beta_4$ Integrins", *The Journal of Cell Biology*, 144(3): 563-574, 1999.

Fukushima, et al., "Integrin α3β1-Mediated Interaction with Laminin-5 Stimulates Adhesion, Migration and Invasion of Malignant Glioma Cells", *Int. J. Cancer*, 76: 63-72, 1998.

Skyldberg, et al., "Laminin-5 as a Marker of Invasiveness in Cervical Lesions", *Journal of the National Cancer Institute*, 91(21): 1882-1887, 1999.

Moriya, et al., "Increased Expression of Laminin-5 and Its Prognostic Significance in Lung Adenocarcinomas of Small Size", *Cancer*, 91(6): 1129-1141, 2001.

* cited by examiner

*Primary Examiner*—Maher M. Haddad
(74) *Attorney, Agent, or Firm*—Choate, Hall & Stewart, LLP (57) ABSTRACT

A method of determining a laminin 5 antigen in a biological sample, comprising the steps of bringing an antibody reactive to a laminin 5 γ2 chain N-terminal fragment into contact with the biological sample; measuring a reaction of the antibody; and determining an amount of the laminin 5 antigen based on a measurement result of the reaction, as well as, a method of detecting a laminin 5-producing tumor cell, a method of examining acute respiratory distress syndrome and a method of evaluating malignancy of a malignant tumor based on the assay method.

2 Claims, 8 Drawing Sheets

Tumor weight and serum LN5 antigen in HPAC-transplanted nude mouse

REAGENT FOR DETERMINING LAMININ 5 ANTIGEN IN BIOLOGICAL SAMPLE AND ASSAY METHOD

TECHNICAL FIELD

The present invention relates to a method and a reagent for determining a laminin 5 antigen in a biological sample.

BACKGROUND ART

A basal lamina is constituted by an extracellular matrix component which is mainly a collagen, and exists universally in an organism. One of macromolecular proteins constituting the basal lamina is laminin (hereinafter, often abbreviated as LN). The LN is classified into more than ten kinds based on the structure thereof, which are different in functions and localized tissues, and is classified by adding a number at the end, e.g., LN1 or LN2. Every LN is constituted by a complex formed from three polypeptide chains each having a different amino acid sequence, and gives a cross-like molecular form in an electron microscope observation. The three polypeptide chains are respectively called $\alpha$ chain, $\beta$ chain, and $\gamma$ chain, and each has several molecular species ($\alpha$1 to $\alpha$5, $\beta$1 to $\beta$3, and $\gamma$1 and $\gamma$2).

In the basal lamia between epithelial cells and a connective tissue backing the epithelial cells, there exists a cell adhesion structure peculiar to the epithelial cells. As an extracellular matrix-constituting protein which exists mainly in the above structure, laminin 5 is known (hereinafter, often abbreviated as LN5). Physiological characteristics of LN5 is that it is the only LN in the above LN group, produced solely from epithelial cells and that it has an activity to promote adhesion to the basal lamia and motility of epithelial cells. As for the epithelial cell, it is known phenomena that it adheres strongly to LN5 and the basal lamia containing LN5 via a specific receptor called integrin on a cell membrane of the epithelial cell itself, and that it migrates aggressively.

The LN5 is constituted by a complex formed from one $\alpha$3 chain, one $\beta$3 chain, and one $\gamma$2 chain. The $\gamma$2 chain, in particular, is considered to be specific to LN5, and is not included in the other LN molecular species [Dev. Dyn., 218, 213-234 (2000)]. In addition, it is found that LN5 is partially degraded by a proteolytic enzyme (protease) when secreted from the epithelial cells, and it is indicated that, especially by shedding an N-terminal part of the $\gamma$2 chain, the remaining molecular entity of LN5 from which the N-terminal part was released has an increased activity for promoting cell movement [J. Cell Biol., 148, 615-624 (2000)].

That is, the amount of LN5 $\gamma$2 chain fragments released from the epithelial cells, etc. reflects an LN5 production amount in the cells, and it considered to be a potential index for measuring an epithelial cell motility-promoting activity of LN5 in an epithelial tissue.

Recently, a lot of study results reported that an expression of the LN5 increased in a malignant tumor tissue from epithelial cells. There are many reports, in particular, that the LN5 expression level correlates well with an invasiveness of a malignant tumor, and its application as a pathological marker for the purpose of in vitro diagnosis of cancer is considered to be possible [J. Natl. Cancer Inst., 91, 1882-1887 (1999) and Cancer, 85, 2315-2321 (1999)].

However, in the above studies, there is mainly employed a method in that a pathologic tissue is removed from a body of a patient through an operation to prepare a section, and then an expression site of a target protein is immunstained with an antibody. Such method lacks quantitativeness and versatility in terms of practical application to in vitro diagnosis in medical places, and also has a problem of imposing physical strains on a patient, for example, a surgical operation and a tissue biopsy. Therefore, an establishment of a simple and quick method of determining a level of an LN5 antigen in a biological sample, such as blood, which can be sampled relatively safely is desired.

Recently, there has been reported an enzyme-linked immunosorbent assay (ELISA) using two kinds of monoclonal antibodies to LN5 (a monoclonal antibody BM165 against an $\alpha$3 chain and a monoclonal antibody 6F12 against a $\beta$3 chain) [J. Immunol. Meth., 224, 161-169 (1999)]. However, this report shows no example that an LN5 antigen in a biological sample is detected by ELISA.

DISCLOSURE OF THE INVENTION

An object of the present invention is to provide a method of determining an LN5 antigen in a small amount of a biological sample accurately and simply, using an antibody that specifically binds to LN5.

The inventors of the present invention focused on the degradation of an LN5 $\gamma$2 chain in various examinations of a method of determining an LN5 antigen in a biological sample. Thus, the inventors of the present invention prepared monoclonal antibodies recognizing respective chains of LN5, and immunologically analyzed an LN5 antigen in culture supernatants of epithelial tumor cells. As a result, it was found that many epithelial tumor cells secreted LN5 with its $\gamma$2 chain shed into culture supernatants thereof. Furthermore, it was confirmed that the prepared monoclonal antibody against the $\gamma$2 chain was reactive to a $\gamma$2 chain fragment released due to the protease degradation of LN5.

As a result of further analyses, a plurality of kinds of monoclonal antibodies reactive to the released $\gamma$2 chain fragment were prepared, to prepare a sandwich-type immunological assay reagent using two different monoclonal antibodies reactive to the $\gamma$2 chain fragment. It was also found that an LN5 antigen in a blood serum and a blood plasma could be determined efficiently by using the assay reagent using two different monoclonal antibodies reactive to the LN5 $\gamma$2 chain fragment.

As explained above, the $\gamma$2 chain is a constituent specific to LN5, and not included in the other LN molecular species. That is, the assay reagent using the antibody against the $\gamma$2 chain fragment allows to determine any molecule of a $\gamma$2 chain fragment, a nonfragmented $\gamma$2 chain, a $\beta$3 chain-$\gamma$2 chain complex, or an $\alpha$3 chain-$\beta$3 chain-$\gamma$2 chain complex in a biological sample. It is therefore considered that the reagent determines most of LN5 antigens and thus may provide a useful index which reflects the LN5-producing amount in an epithelial tissue for grasping a pathological condition.

It was also experimentally examined what kind of in vivo phenomena an increase of an LN5 antigen in a biological sample reflects. Eleven kinds of human pancreatic tumor cell lines were cultured in a liquid medium in the presence of a 10% bovine fetal serum for a given period, and LN5 concentrations in the culture supernatants and expression levels of various integrins which are adhesion molecular receptors expressed were compared. Six kinds of LN5-producing lines obviously had a tendency to express higher expression level of $\beta$4 integrin in comparison to five kinds of LN5-nonproducing lines. That is, it was experimentally proved that the in vivo LN5 antigen-producing amount may be an index for the $\beta$4 integrin expression level in epithelial cells in an in vivo epithelial tissue.

Further, a human tumor producing LN5 was transplanted to a nude mouse and it was thus found that a growth of the tumor and the LN5 concentration in a blood serum correlated each other, thereby elucidating that determining LN5 in a blood serum allows monitoring of the growth of an LN5-producing tumor.

In addition, it was hypothesized that an LN5 metabolism in an organism increases in pulmonary inflammatory disease, based on the fact that much LN5 is included especially in a pulmonary epithelial tissue among organs in an organism. Under the hypothesis, the LN5 antigen concentration in blood plasma specimens sampled from patients suffering from acute respiratory distress syndrome (hereinafter, abbreviated as ARDS) and in blood plasma specimens sampled from healthy subjects was determined in accordance with the above method. It was found that the concentration in blood was obviously higher for a group of the patients suffering from acute respiratory distress syndrome, in comparison with the group of healthy subjects, thereby discovering that the method was extremely useful for clinical diagnosis of the disease.

The present invention was completed based on the above findings. That is, the present invention provides the following.

1. A method of determining a laminin 5 antigen in a biological sample, comprising the steps of:
   bringing an antibody reactive to a laminin 5 γ2 chain N-terminal fragment into contact with the biological sample;
   measuring a reaction of the antibody; and
   determining an amount of the laminin 5 antigen based on a measurement result of the reaction.

2. A method according to item 1, wherein the antibody is a monoclonal antibody produced from a cell deposited with an accession number of FERM BP-8136, FERM BP-8133, or FERM BP-8134.

3. A reagent for determining a laminin 5 antigen in a biological sample, comprising an antibody reactive to a laminin 5 γ2 chain N-terminal fragment.

4. A reagent for determining a laminin 5 antigen according to item 3, wherein the antibody is a monoclonal antibody produced from a cell deposited with an accession number of FERM BP-8136, FERM BP-8133, or FERM BP-8134.

5. A monoclonal antibody produced from a cell deposited with an accession number of FERM BP-8136, FERM BP-8133, or FERM BP-8134.

6. A method of detecting a laminin 5-producing tumor cell, comprising the steps of:
   determining a laminin 5 antigen in a biological sample by the method as defined in item 1 or 2; and
   detecting a laminin 5-producing tumor cell based on an assay result of the laminin 5 antigen.

7. A detection reagent for detecting a laminin 5-producing tumor cell, comprising the reagent for determining as defined in item 3 or 4.

8. A method of examining acute respiratory distress syndrome, comprising the steps of:
   determining a laminin 5 antigen in a biological sample by the method as defined in item 1 or 2; and
   examining acute respiratory distress syndrome based on an assay result of the laminin 5 antigen.

9. An examination reagent for examining acute respiratory distress syndrome, comprising the reagent for determining as defined in item 3 or 4.

10. A method of evaluating malignancy of a malignant tumor, comprising the steps of:
    determining a laminin 5 antigen in a biological sample by the method as defined in item 1 or 2; and
    evaluating malignancy of a malignant tumor based on an assay result of the laminin 5 antigen.

11. An examination reagent for evaluating malignancy of a malignant tumor, comprising the reagent for determining as described in item 3 or 4.

12. A method of determining β4 integrin expression, comprising the steps of:
    bringing an antibody reactive to a laminin 5 into contact with a cell culture supernatant;
    measuring a reaction of the antibody; and
    determining an expression level of a β4 integrin in the cell based on the measurement result of the reaction.

BEST MODE FOR CARRYING OUT THE INVENTION

An LN5 γ2 chain N-terminal fragment in the present description refers to an N-terminal side fragment among the fragments generated by degradation of a γ2 chain. The N-terminal fragment is usually a fragment which may be released into a biological sample, i.e., a fragment which may exist in a biological sample, which is a liquid sample, or in a liquid fraction prepared from a biological sample. Examples of such an N-terminal fragment include a fragment of a molecular weight of about 50,000, containing the domains IV and V of the γ2 chain.

An antibody reactive to an LN5 γ2 chain N-terminal fragment in the present description refers to an antibody that is immunochemically bound to an LN5 γ2 chain N-terminal fragment, i.e., an antibody showing an antigen-antibody reaction.

A biological sample in the present description is a body fluid such as a blood serum, a blood plasma, cerebrospinal fluid, ascites, urine, tears, sweat, or saliva, excrement, tissue extract, etc. There is no particular limitation provided that the biological sample is normally sampled at a medical institution, etc., but a blood specimen from a subject, such as a blood serum or a blood plasma is particularly preferable.

An LN5 antigen in the present description is an antigen with which an antibody reactive to an LN5 γ2 chain N-terminal fragment reacts immunochemically, and includes an LN5 γ2 chain and an N-terminal fragment thereof and a complex including a γ2 chain.

The step of bringing a biological sample into contact with an antibody reactive to an LN5 γ2 chain N-terminal fragment, the step of measuring the reaction of the antibody, and the step of determining a level of the LN5 antigen based on a measurement for the reaction, in the method of determining an LN5 antigen in a biological sample of the present invention, may be similar to those in a method of determining an antigen using a general immunochemical method, except using an antibody reactive to an LN5 γ2 chain N-terminal fragment as the antibody.

In the assay method of the present invention, an LN5 γ2 chain N-terminal fragment which is degraded to be secreted in a body fluid and thereby can be determined in a biological sample, is preferably determined by means of an immunochemical method using an antibody, reactive to the LN5 γ2 chain N-terminal fragment preferably a monoclonal antibody, more preferably a monoclonal antibody produced from a cell deposited with an accession number of FERM BP-8136, FERM BP-8133, or FERM BP-8134.

Examples of the immunochemical method include, but not particularly limited to, a latex agglutination method, a competition method, and a sandwich method. In the competition method and the sandwich method, an LN5 antigen or an antibody is labeled with a labeling substance such as a radioactive label, an enzyme label, an electrochemiluminescence (ECL) label, or a fluorescence label to be detected by a method suitable to the label. Preferably, the sandwich method using an antibody labeled with an enzyme label or an electrochemiluminescence label, more preferably, the sandwich method using an antibody labeled with an electrochemiluminescence label is suitable.

An assay reagent of the present invention, which is an assay reagent used in the assay method of the present invention, includes at least an antibody reactive to the LN5 γ2 chain N-terminal fragment, preferably a monoclonal antibody, more preferably a monoclonal antibody produced from a cell deposited with an accession number of FERM BP-8136, FERM BP-8133, or FERM BP-8134, and may optionally include a standard antigen of LN5 and a detection reagent for a label depending on the kind of the label, e.g., an enzyme substrate in case of the enzyme label. The assay reagent may also include an appropriate buffer. An antibody may be bonded to a carrier or a label acceptable for use in an assay reagent to form an immobilized antibody or a labeled antibody. The assay reagent of the present invention may be manufactured by selectively using a technique generally used for manufacturing a reagent containing an antibody. In the case that the assay reagent is composed of a plurality of constituents, the reagent may be in a kit.

The antibody reactive to the LN5 γ2 chain N-terminal fragment is not particularly limited provided that the antibody is the one having an ability to bind to the LN5 γ2 chain N-terminal fragment, such as a polyclonal antibody derived from an antiserum obtained by immunizing a purified LN5 γ2 chain fragment with an experimental animal. However, a mouse monoclonal antibody is the best because of its excellent reaction specificity and its inexpensive manufacturing cost.

The method of preparing a monoclonal antibody will be explained below. A human LN5 may be purified in accordance with a method already reported (Int. J. Cancer, 76, 63-72 (1998)). The purified LN5 or the purified LN5 γ2 chain fragment is dissolved in a saline as an immunological antigen to be administered to an experimental animal with an appropriate adjuvant. Examples of the experimental animal include one available from a breeder, and especially a Balb/C mouse may be frequently used, but not limited thereto. The administration of the antigen is repeated several times at intervals of several weeks. At 3 days after the last administration, the spleen is extracted from the immunized animal. The extracted spleen is dispersed into single cells, which are subjected to cell fusion with pre-cultured mouse myeloma cells in the presence of a polyethylene glycol reagent. After the cell fusion, selective culture using a drug is conducted to select only a hybridoma cell producing a monoclonal antibody reactive to the LN5 γ2 chain N-terminal fragment. After that, several times of cloning operations of an antibody-producing cell bring about a complete monoclonal antibody-producing cell. The specificity of the monoclonal antibody can be identified, for example, by a Western blot analysis, etc. of the purified antigen used for immunization which is separated by electrophoresis [Antibodies: a Laboratory Manual, by Ed Harlow & D. Lane, Cold Spring Harbar Laboratory Press (1988)].

The antibody produced from the cell deposited to International Patent Organism Depositary of National Institute of Advanced Industrial Science and Technology with the accession number of FERM BP-8136, FERM BP-8133, or FERM BP-8134 may be used as the monoclonal antibody.

The ECL method will be explained below. While various measurement methods are known for the ECL measurement of an LN5 antigen in a biological sample, as one having remarkable simplicity and high quantitativeness, the sandwich method simultaneously using a first antibody-immobilized magnetic bead and a second antibody labeled with a ruthenium complex is preferable. In this case, the first antibody and the second antibody desirably bind to different antigenic determinants respectively while the antibodies specifically react to the LN5 γ2 chain fragment.

The standard antigen may be prepared by purifying a human tumor cell line, e.g., a culture supernatant of a human tumor cell line and then by determining its protein concentration by absorbance analysis, etc., and may be used by being diluted with a diluent to an appropriate concentration on use.

An example of the assay procedure will be explained below, but the present invention is not limited thereto.

An LN5 γ2 chain fragment antibody (the first antibody) is immobilized on a commercially available magnetic bead. The immobilization may be via a covalent bond or a noncovalent bond. Then, for inhibiting nonspecific binding of other molecules with the magnetic bead, a blocking protein such as milk casein is adsorbed to the beads.

A standard LN5 antigen solution, the concentration of which is known in advance, or a subjective biological sample is then added thereto and the whole is stirred for a given time. After the LN5 antigen in the sample is adsorbed to the surface of an antibody-bound particle, the particle is washed. Next, another anti-LN5 γ2 chain fragment antibody (the second antibody) labeled with a chemiluminescent complex such as ruthenium is added in an appropriate concentration. The sample is stirred for a given time to form a complex of the first antibody, the LN5 antigen, and the second antibody on the magnetic bead.

Then, after the bead has been washed, the bead is placed between a pair of electrodes in a special device and is charged with electricity to make the complex as a marker emit light for measuring the emission intensity. At this point, an emission level corresponding to the level of the ruthenium marker is obtained. Comparison of the emission level of the subjective biological sample with the emission level of the standard sample using a calibration curve, etc. allows one to know the LN5 antigen level in the subjective biological sample accurately.

The method of detecting an LN5-producing tumor cell, the method of examining acute respiratory distress syndrome, and the method of determining the malignancy of a malignant tumor of the present invention are characterized by determining an LN5 antigen in a biological sample, to conduct detection, examination, and determination based on the assay result.

The assay of the LN5 antigen in a biological sample is conducted in accordance with the assay method of the present invention. Using the assay result for the LN5 antigen as an index allows to detect an LN5-producing tumor cell, to examine acute respiratory distress syndrome, and to determine the malignancy of a malignant tumor. For example, if the quantitative level of the LN5 antigen is higher than the normal value, it may be recognized that an LN5-producing tumor cell is detected, that acute respiratory distress syndrome is detected, and that the malignancy of a malignant tumor is determined to be high.

The assay reagent of the present invention may be used in applications including detection of an LN5-producing tumor cell, examination of acute respiratory distress syndrome, and determination of the malignancy of a malignant tumor.

The present invention also provides a method of determining the β4 integrin expression of a cell. The method includes the steps of: bringing a cell culture supernatant into contact with an antibody reactive to an LN5; measuring the reaction of the antibody; and determining an expression level of a β4 integrin in the cell based on the measurement for the reaction.

The step of bringing a cell culture supernatant into contact with an antibody reactive to an LN5 and the step of measuring the reaction of the antibody may be similar to those of the method of determining the antigen using a general immunochemical method, except using an antibody reactive to LN5. The immunochemical method may be similar to that explained above for the assay method of the present invention.

The antibody reactive to LN5 is preferably a monoclonal antibody. Examples of such a monoclonal antibody include a monoclonal antibody produced from a cell deposited with an accession number of FERM BP-8133, FERM BP-8134, FERM BP-8135, FERM BP-8136, FERM BP-8137, or FERM BP-8140.

The measurement of the reaction of the antibody reactive to LN5 reflects the LN5-producing level in a culture supernatant, and the β4 integrin expression level is determined by using the measurement as an index.

EXAMPLES

The present invention will be described in reference with detailed examples hereinafter, but is not limited thereto.

Example 1

Preparation of Monoclonal Antibody Against LN5

The human LN5 was purified in accordance with a method already reported [Int. J. Cancer, 76, 63-72 (1998)]. Specifically, a human breast tumor cell line MKN45 (obtained from Japan Cancer Research Resources Bank) was cultured in a liquid medium containing a 2.5% bovine fetal serum and 100 ng/mL phorbol 12-myristate 13-acetate (manufactured by from Wako Pure Chemical Industries, Ltd.). Then, a culture supernatant was sampled, followed by removing cell components by centrifugation. After that, a protease inhibitor was added to the supernatant. The culture supernatant was applied to a column packed with a gel to which an anti-LN5 γ2 chain polyclonal antibody was immobilized, followed by sufficiently washing with a phosphate buffer saline (PBS). The LN5 bound to the column was eluted using a 0.1 M glycine-hydrochloride buffer (pH 3.0). The LN5 eluted from the column was promptly neutralized and was then sufficiently dialyzed against PBS in a dialysis tube. The LN5 preparation thus purified was analyzed by polyacrylamide electrophoresis to identify the presence of an α3 chain, a β3 chain, and a γ2 chain.

The purified LN5 was intraperitoneally administered to Balb/C female mice (6 weeks of age) in an amount of 0.015 mg per mouse with Complete Freund's Adjuvant (manufactured by Sigma Aldrich Corporation). After 3 weeks, the same amount of LN5 was intraperitoneally administered with Incomplete Freund's Adjuvant (manufactured by Sigma Aldrich Corporation).

After an additional 3 weeks, only purified LN5 was administered to the mice in an amount of 0.03 mg per mouse. After 3 days from the last immunization, spleens were removed from the mice. The operations after that were conducted in a clean bench. The removed spleens were dispersed using a mesh, and were mixed with pre-cultured Sp2/0-Ag14 mouse myeloma cells, followed by cell fusion in the presence of 50% polyethylene glycol 1500 (manufactured by Boehringer Mannheim). The fused hybridoma cells were separated into several 96-well microculture plates and were cultured in an RPMI1640 liquid medium containing a 10% bovine fetal serum and an HAT reagent (manufactured by ICN Biomedicals Inc.) for 1 to 2 weeks. During this period, only a hybridoma cell stably producing a monoclonal antibody survived while the nonfused myeloma cells and mouse spleen cells were dead.

The cell producing a monoclonal antibody against LN5 was selected by ELISA using an antigen-immobilized plate. Specifically, a culture supernatant was sampled at the time when a colony of a hybridoma cell had sufficiently grown, and was added into a 96-well microplate (manufactured by Nalge Nunc International) to which an immunogen adsorbed in an immobilized phase, to be allowed to react with the monoclonal antibody in the supernatant. A peroxidase conjugate of the second antibody reactive to a mouse IgG (manufactured by American Qualex, Inc.) was then added to the supernatant in an appropriate concentration. The plate was washed after a given period of time, and then a solution of o-phenylenediamine enzyme substrate color developer (manufactured by Wako Pure Chemical Industries, Ltd.) and hydrogen peroxide was added. Four lines of the target monoclonal antibody-producing hybridoma were selected based on the presence or absence of color development. The selected 4 lines were cloned several times and were named 19, 57, 8C2, and 2B10. The large scale manufacture of each monoclonal antibody was carried out according to an ordinary method by intraperitoneally inoculating the hybridoma to a mouse, and then by purifying the antibody from ascites of the mouse by affinity chromatography using protein G fixed Sepharose gel (manufactured by Pharmacia).

The obtained monoclonal antibody was examined for specificity using LN5 produced from a human breast carcinoma cell line MKN45, a human glioblastoma cell line A-172, a human leiomyosarcoma cell line HT-1080, and a human epidermal carcinoma cell line A-431. The A-172 cell was obtained from American Type Culture Collection, and the HT-1080 cell and the A-431 cell were obtained from Japan Cancer Research Resources Bank.

Figure 1:
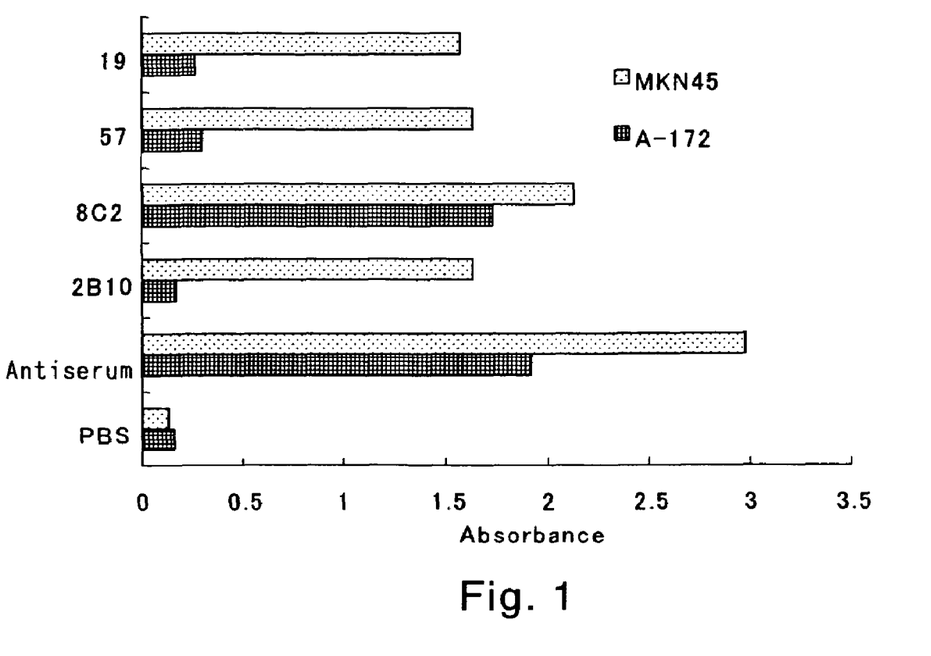
FIG. 1 is a graph showing reactivity of each of monoclonal antibodies (19, 57, 2B10, and 8C2) to LN5 from culture mediums of MNK45 cells and A-172 cells. The term "antiserum" refers to a reaction of anti-human LN5 mouse polyclonal antibody. The term "PBS" refers to a reaction without addition of an antibody. The horizontal axis of the graph indicates an absorbance value in ELISA.

Each cell was cultured in a tissue culture flask using an RPMI 1640 medium containing a 10% bovine fetal serum, and a culture supernatant was sampled. LN5 was purified from the culture supernatant by the above-mentioned method. The cell line A-172 is known to secret a γ2 chain singly, and the purified LN5 mainly contains the γ2 chain. On the other hand, the LN5 from the culture supernatant of the MKN45 cell contains each of the α3 chain, the β3 chain, and γ2 chain in approximately the same amount. The reactivity of the 4 monoclonal antibodies to the two kinds of LN5s was compared by ELISA in accordance with the above-described method. As a result, because only 8C2 strongly reacted with the two, the 8C2 monoclonal antibody was found to recognize the LN5 γ2 chain (FIG. 1).

Furthermore, when culturing each of the cell lines HT-1080 and A-431, secreted proteins were labeled with an express $^{35}S$ protein labeling mix reagent (manufactured by NEN Life Science). The culture supernatant was subjected to immunoprecipitation of antigen proteins using the 4 monoclonal antibodies. Specifically, to a given amount of the $^{35}S$-labeled cell culture supernatant, an antibody was added and further a gel to which an anti-mouse IgG antibody was immobilized was added. After stirring gently for a while, the gel was separated by low-speed centrifugation and was heated as it was in an SDS-containing sample solution, followed by separating the antigen protein adsorbing to the gel by electrophoresis.

Figure 2:
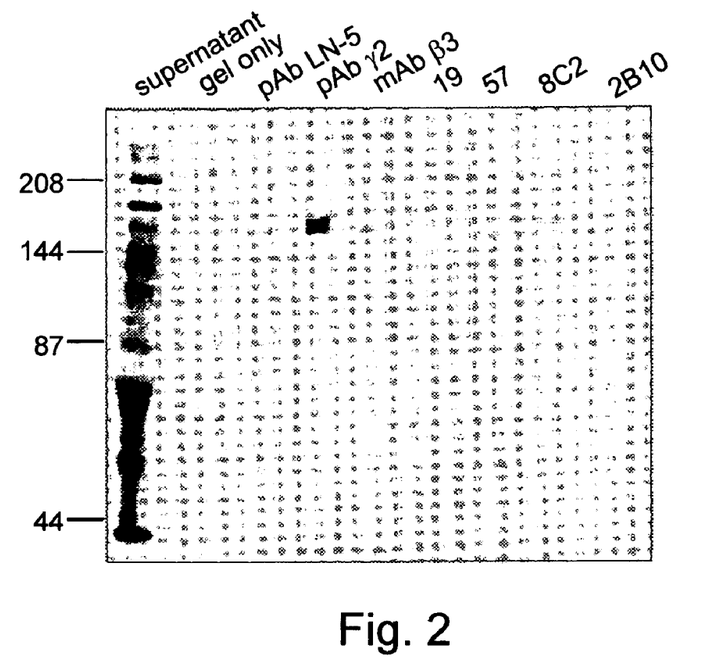
FIG. 2 shows a result of an immunoprecipitation experiment of the LN5 antigen in an HT-1080 cell culture medium using each antibody. Numerical values in left indicate migration positions of a molecular weight marker (kDa). The term "supernatant" refers to a migration image of total proteins. The term "gel only" refers to a migration image of proteins from gel used in the immunoprecipitation. The term "pAb LN-5" refers to a migration image of proteins imminoprecipitated using a polyclonal antibody to human LN5. The term "pAb γ2" refers to a migration image of the proteins immunoprecipitated using a polyclonal antibody to human LN5 γ2 chain. The term "mAb β3" refers to a migration image of the proteins immunoprecipitated using a monoclonal antibody to a human LN5 β3 chain.
Figure 3:
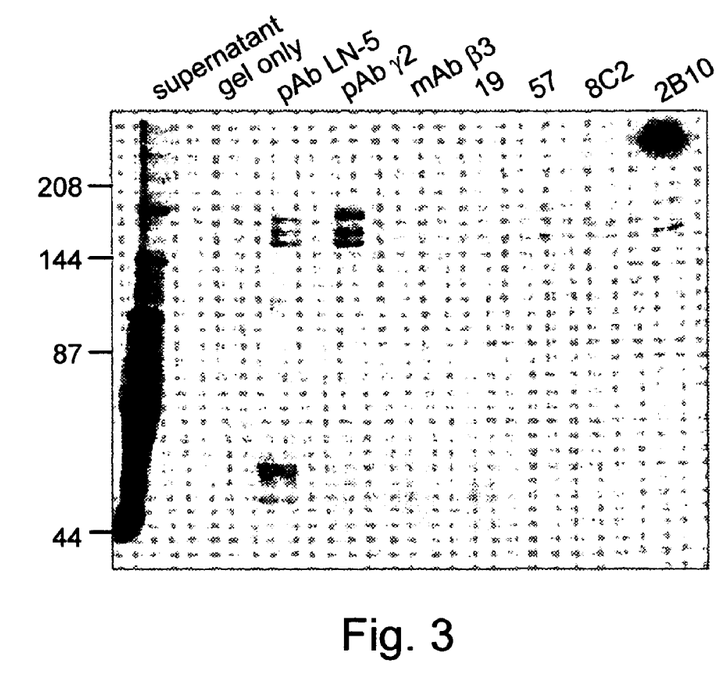
FIG. 3 shows a result of an immunoprecipitation experiment of the LN5 antigen in an A-431 cell culture medium using each antibody. Numerical values in left indicate migration positions of a molecular weight marker (kDa). The term "supernatant" refers to a migration image of total proteins. The term "gel only" refers to a migration image of proteins from gel used in the immunoprecipitation. The term "pAb LN-5" refers to a migration image of proteins imminoprecipitated using a polyclonal antibody to human LN5. The term "pAb γ2" refers to a migration image of the proteins immunoprecipitated using a polyclonal antibody to human LN5 γ2 chain. The term "mAb β3" refers to a migration image of the proteins immunoprecipitated using a monoclonal antibody to a human LN5 β3 chain.

The cell line HT-1080 is known to express no α3 chain and to secrete a complex of a β3 chain and a γ2 chain. On the other hand, the cell line A-431 is known to express all the chains. As a result of the electrophoresis analysis for the immunoprecipitate, both of the 19 and the 57 strongly reacted with the antigen (β3 chain), which migrated to a position of a molecular weight of around 145 kDa, from an HT-1080 supernatant. While, the 8C2 strongly reacted with the antigen (γ2 chain), which migrated to a position of a molecular weight of around 155 kDa, from the HT-1080 supernatant (FIG. 2). The 2B10 reactive antigen was not detected in the HT-1080 supernatant. Any of the 4 monoclonal antibodies precipitated a 3-chain complex of the α3 chain, the β03 chain, and the γ2 chain from the A-431 cell culture supernatant (FIG. 3).

The above experimental results elucidated that the 19 and the 57 reacted with the β3 chain, that the 2B10 reacted with the α3 chain, and that the 8C2 reacted with the γ2 chain. Because both of the 19 and the 57 reacted with the β3 chain similarly, only the 57 was used in the examination below.

Example 2

Determining the LN5 Level in Human Tumor Cell Culture Supernatant Using Monoclonal Antibody Eleven human pancreatic tumor cell lines (KP-1, KP-2, KP-3, KP-4, AsPC-1, HPAC, SUIT-2, MIApaca-II, PSN-1, BxPC-3, PANC-1:MIApaca-II (CRL-1420), PANC-1 (CRL-1469), AsPC-1 (CRL-1682), and HPAC (CRL-2119) were obtained from ATCC. The KP-1 to KP-4, the SUIT-2, and the BxPC-3 were gratefully given from Dr. Akihiro Funakoshi of National Kyushu Cancer Center. The PSN-1 was gratefully given from Dr. Kazuto Nishio of National Cancer Center) were cultured in an RPMI-1640 medium supplemented with a 10% bovine fetal serum in a culture flask, to sample the culture supernatant thereof at a stage of sufficient growth of the lines. The culture supernatant was aseptically sealed and stored at 4° C. until use.

Among the 3 monoclonal antibodies (57, 2B10, and 8C2) which were prepared and the specificity of which was identified in Example 1, the 57 and 2B10 monoclonal antibodies were labeled with horseradish peroxidase (manufactured by Boehringer Mannheim) by a periodate method. Each of the labeled monoclonal antibodies was sufficiently dialyzed against PBS, was filter-sterilized using a membrane filter (manufactured by Nihon Millipore), and was then stored at 4° C. The purified monoclonal antibody of 57 or 8C2 was diluted with PBS to a concentration of 0.01 mg/mL and was added in an amount of 0.2 mL to each well of a MAXISOAP 96-well microplate (manufactured by Nalge Nunc International K. K.) to immobilize each antibody. Those plates were sealed so as not to be dried and stood at 4° C. for 12 hours or more. Then, the antibody solution in the plate was discarded, and a 1% skimmed milk-containing PBS solution was added into each well in an amount of 0.2 mL, followed by standing for 1 hour to block the plate.

A human LN5 standard sample (derived from the MKN45 cell) was diluted with a 1% skim milk-containing PBS solution to prepare solutions having concentrations of 1000, 500, 250, 125, 62.5, 31.25, and 15.625 ng/mL. The blocking solution was discarded from the antibody-immobilized plate in which the blocking was completed. Then, each of the human LN5 level standard samples and already sampled 11 human pancreatic tumor cell culture supernatants was added into a well in an amount of 0.1 mL. After standing at room temperature for 2 hours, the solution was discarded and the wells were washed with PBS sufficiently. The peroxidase-conjugate of the monoclonal antibody 57 or 2B10 described above was appropriately diluted with a 1% skim milk-containing PBS to add into each well in an amount of 0.1 mL. After standing at room temperature for 2 hours, the solution was discarded, and the wells were sufficiently washed with PBS. An ABTS enzyme substrate solution (manufactured by Roche Diagnostics K. K.) was added to each well in an amount of 0.1 mL and was stood at room temperature for 10 minutes with stirring sometimes. A 2 mM aqueous solution of sodium azide was additionally added to each well in an amount of 0.1 mL, followed by sufficiently mixing to terminate the reaction. The absorbance at 492 nm of each well was measured using the T-max microplate reader (manufactured by Molecular Devices Corporation) and a calibration curve was made based on the absorbance of the standard sample, to calculate the LN5 level in each culture supernatant.

Figure 4:
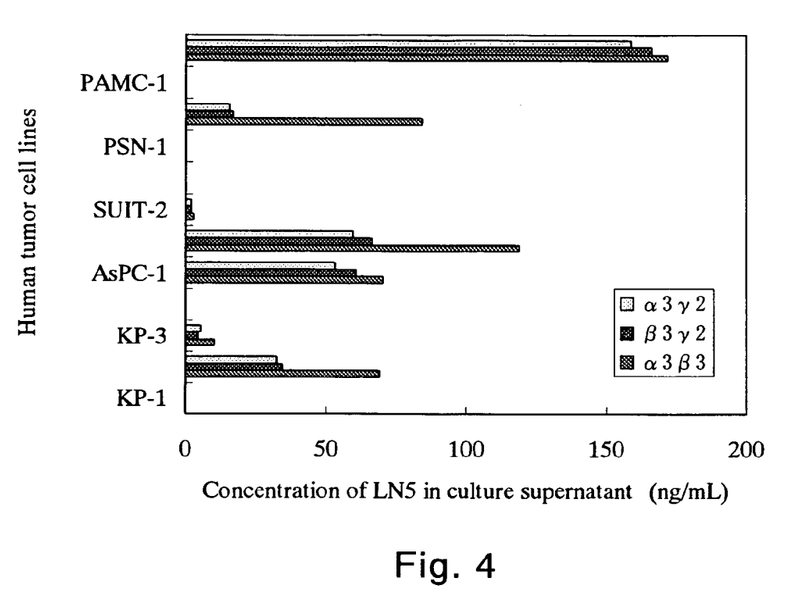
FIG. 4 shows a measurement result of LN5 concentration in culture supernatants of eleven kinds of human pancreatic tumor cell lines and an MKN45 human gastric tumor cell line. The term "α3γ2" refers to values measured by ELISA using a combination of an 8C2 (anti-g2 monoclonal antibody)-immobilized plate and an enzyme-labeled 2B10 (anti-α3 chain monoclonal antibody). The term "β3γ2" refers to values measured by ELISA using a combination of an 8C2 (anti-γ2 monoclonal antibody)-immobilized plate and an enzyme-labeled 57 (anti-β3 chain monoclonal antibody). The term "α3β3" refers to values measured by ELISA using a combination of a 57 (anti-β3 monoclonal antibody)-immobilized plate and an enzyme-labeled 2B10 (anti-α3 chain monoclonal antibody).

As a result of the measurement, the LN5 production in a part of the human pancreatic tumor cell lines was confirmed, and the LN5 measured value by ELISA using the 8C2 monoclonal antibody as an immobilized antibody was obviously lower than the LN5 measured value by ELISA not using the 8C2 monoclonal antibody (FIG. 4). However, in the culture supernatant of the cell line MKN45, such tendency as value-decreasing was not detected. The MKN45-derived LN5 is known not to fragment at the γ2 chain thereof, so that the 8C2 was considered to have reaction specificity to a fragment site of the γ2 chain to be released.

Also, the 11 kinds of human pancreas cancer culture cells were collected from the flasks with a trypsin treatment simultaneously with the sampling of the culture supernatant. After the cell number had been counted, the cells were added into microtubes with the same cell number respectively. To the respective tubes, the monoclonal antibodies against the human α1-, α2-, α3-, α5-, α6-, β1-, β3-, and β4 integrins (all manufactured by CHEMICON International, Inc.) were added, and the tubes were stood for 30 minutes with ice-cooling, followed by washing the cells with PBS. To the tubes, the FITC-labeled second antibody were further added and the tubes were stood again for 30 minutes with ice-cooling. Finally, after washing with PBS, a 1% paraformaldehyde fixing solution was added to fix the cell surface antigen. Each fixed cell suspension was passed through the FACScan cell analyzer (manufactured by Nippon Becton Dickinson Company Ltd.) to measure the fluorescence intensity mean value of the cell surface, thereby determining each integrin expression level in the surface of a cell membrane. The fluorescence intensity mean value was represented as a ratio to the background mean value (Relative Mean Fluorescence).

Figure 5:
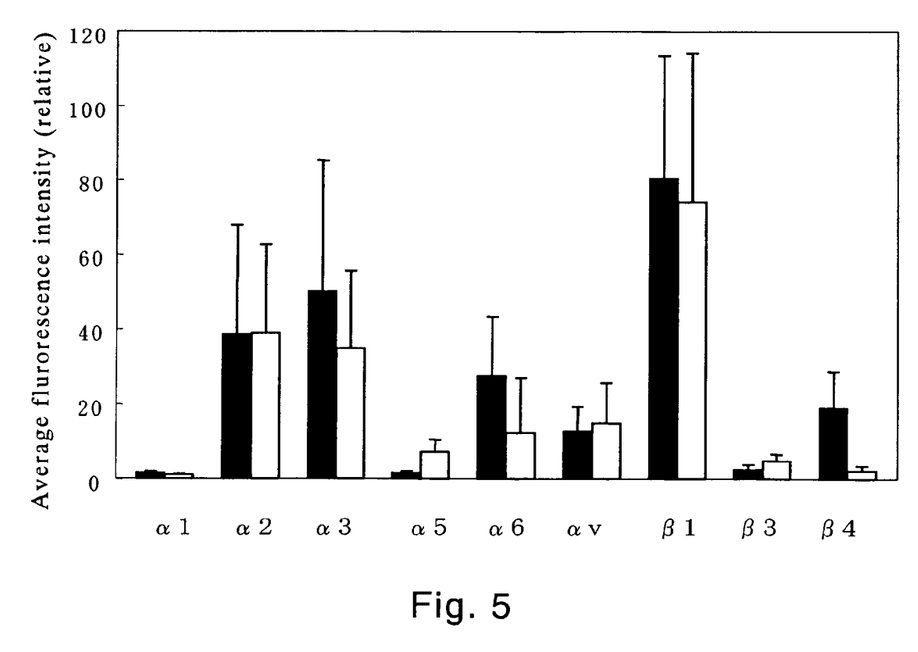
FIG. 5 shows a result of comparing an expression level of each integrin molecule from eleven kinds of the human pancreatic tumor cell lines. There are shown the mean value and standard deviation of each integrin expression level of the LN5-producing lines (KP-2, KP-3, AsPC-1, HPAC, SUIT-2, and BxPC-3) and the mean value and standard deviation of each integrin expression level of the LN5-nonproducing lines (KP-1, KP-4, MIApaca-II, PSN-1, and PANC-1).

Among the 11 human pancreatic tumor cell lines, the integrin expression of the 6 LN5-producing lines and the 5 LN5-nonproducing lines were compared (FIG. 5). While the expression of β1 integrin, etc. in the LN5-producing lines was approximately in equal to that in the LN5-nonproducing lines, the expression of β4 integrin in the LN5-producing lines obviously increased. This indicates that the production level of LN5 may be an index for β4 integrin expression.

Example 3

Preparation of Monoclonal Antibody to Degraded Fragment of γ2 Chain (1) Purification of Degraded Fragment of γ2 Chain A purified 8C2 monoclonal antibody was cross-linked to a bromcyan-activated Sepharose (manufactured by Pharmacia) in accordance with an instruction manual to prepare an antibody-immobilized gel. A human pancreatic tumor cell line KP-2 or BxPC-3 was cultured in a large amount in an RPMI-1640 liquid medium containing a 10% bovine fetal serum in a tissue culture flask. After sufficient cultivation, 1 L of the culture supernatant thereof was sampled and centrifuged to remove cell components. The culture supernatant was diluted with PBS and was then applied to a column packed with the 8C2 monoclonal antibody-immbolized gel. After the column had been sufficiently washed with PBS, the LN5 antigen bound to the column was eluted with 8 M urea-containing PBS. The eluted fraction was dialyzed against PBS in a dialysis tube to remove urea. After a sufficient dialysis, the fraction was concentrated using a Centricon centrifugal concentrator (manufactured by Amicon), thereby preparing a purified human LN5 antigen.

Figure 6:
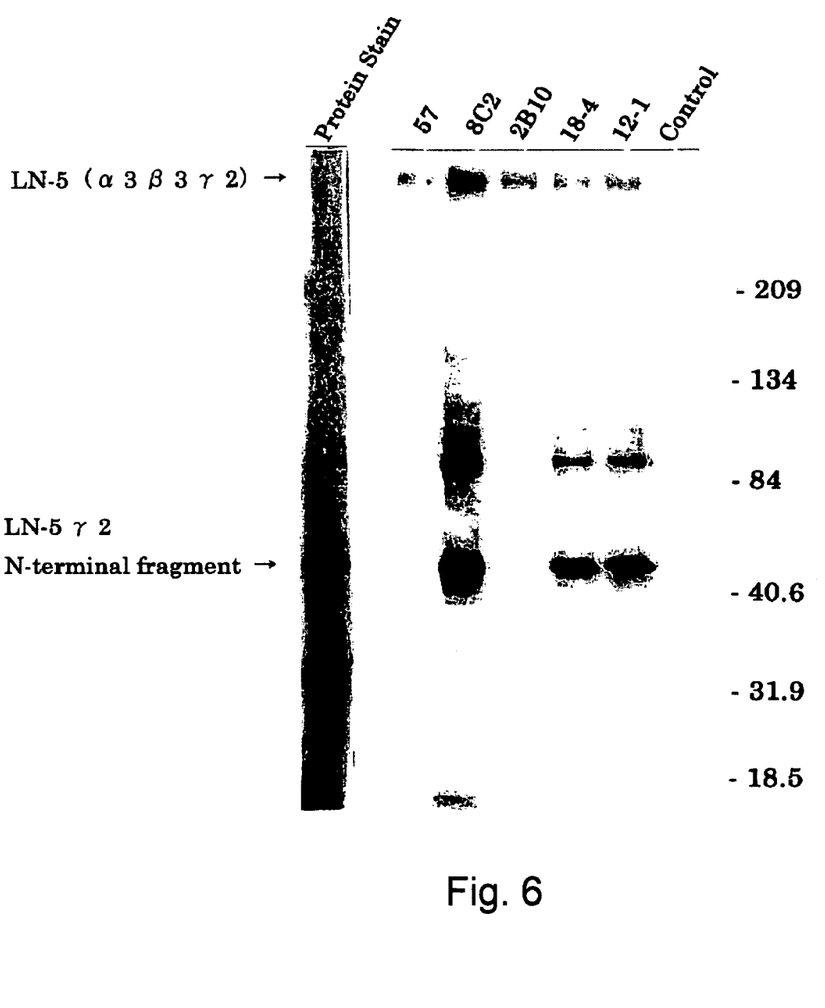
FIG. 6 shows a result of a Western blot experiment of the LN5 antigen in a BxPC-3 cell culture medium using each monoclonal antibody. Numerical values in right refer to migration positions of a molecular weight marker (kDa). The term "8C2" refers to a reactive antigen by the 8C2 monoclonal antibody; the term "2B10" refers to a reactive antigen by the 2B10 monoclonal antibody; the term "18-4" refers to a reactive antigen by the KP2-LN5-8C2E 18-4 monoclonal antibody; the term "12-1" refers to a reactive antigen by the KP2-LN5-8C2E 12-1 monoclonal antigen; and the term "control" refers to a reactive antigen by a control antibody. The three kinds of 8C2, KP2-LN5-8C2E 12-1, and KP2-LN5-8C2E 18-4 are obviously reactive to a fragment having a molecular weight of about 50,000.

The purified product was separated by 4 to 20% gradient-SDS polyacrylamide electrophoresis (manufactured by Daiichi Pure Chemicals Co., Ltd.). The gel was protein-stained using a quick CBB stain solution (manufactured by Wako Pure Chemical Industries, Ltd.) to analyze the molecular weight of the LN5 antigen. Additionally, the LN5 antigen was electrically transferred from the electrophoresed gel to an Immobilon-P membrane (manufactured by Nihon Millipore) and was immuno-stained with the 8C2 monoclonal antibody (FIG. 6). The degraded product to which the 8C2 monoclonal antibody reacted had an estimated molecular weight of around 50,000, and was considered to be a fragment derived from an N-terminal (N-terminal fragment) of a γ2 chain, which was suggested to be released by a proteolytic cleavage in a previous report (Science, 277, 225-228 (1997)). The purified human LN5 γ2 chain N-terminal fragment obtained here was separated in tubes without preservatives and was stored under freezing untill use.

(2) Preparation of Monoclonal Antibody to Decgraded Fragment of γ2 Chain

A novel monoclonal antibody was prepared using the freeze-stored purified γ2 chain N-terminal fragment derived from a KP-2 cell as an immunogen. The preparation of the monoclonal antibody was conducted in accordance with the method described in Example 1. Newly obtained were two kinds of monoclonal antibodies KP2-LN5-8C2E 12-1 (hereinafter, abbreviated as 12-1) and KP2-LN5-8C2E 18-4 (hereinafter, abbreviated as 18-4). It was confirmed by a Western blot analysis that both the monoclonal antibodies were reactive to the γ2 chain fragment having a molecular weight of around 50,000 similarly to 8C2 (FIG. 6).

Each monoclonal antibody was manufactured in a large amount by obtaining a culture supernatant of a hybridoma cell using a Hybridoma-SFM serum-free medium (manufactured by GIBCO Industries, Inc.) and conducting affinity purification using a protein A-immobilized gel. It was confirmed by a Mouse-Typer Isotyping Panel reagent (manufactured by Bio-Rad Laboratories, Ltd.) that the obtained monoclonal antibodies were each of an IgG1 type.

The obtained monoclonal antibody-producing cells (12-1, 18-4, 2B10, 8C2, 19, and 57) were deposited to International Patent Organism Depositary of National Institute of Advanced Industrial Science and Technology (address: AIST Tsukuba Central 6, 1-1-1 Higashi, Tsukuba, Ibaraki, Japan, 305-8566) with the accession numbers of FRPM P-18465, FRPM P-18466, FRPM P-18467, FRPM P-18468, FRPM P-18469, and FRPM P-18470, respectively, on Aug. 16, 2001, and were converted to international accession under the Budapest Treaty on Aug. 1, 2002 (Aug. 5, 2002 for 57), being given the accession numbers of FERM BP-8133, FERM BP-8134, FERM BP-8135, FERM BP-8136, FERM BP-8137, and FERM BP-8140, respectively.

(3) Assay of LN5 Degraded Products in Biological Sample

The two kinds of LN5 γ2 chain monoclonal antibodies obtained in (2) (12-1 and 18-4) were prepared as purified IgGs.

The 18-4 monoclonal antibody purified product was diluted with PBS to a final concentration of 0.2 mg/mL. A suspension (0.25 mL) of Dynabeads M-450 epoxyl (manufactured by Dynal Biotech) was added to 1 mL of the antibody solution, and sealed in a polypropylene container followed by gently stirring at room temperature for 4 hours. The mixture was then stood at 4° C. for around 12 hours for stabilization of the bonds. Then, 2 mL of a PBS solution containing 1% skim milk, 0.1% sodium azide, and 2 mM EDTA (hereinafter, abbreviated as SM/PBS) was added to the antibody-bound beads, for the purpose of blocking the surplus binding sites in the bead surfaces. The mixture was stood as it was for around 12 hours to stabilize the blocking. Then, the beads were washed twice with PBS and was diluted with the SM/PBS solution in 20-fold and stored in a liquid state at 4° C. until use.

A solution of 12-1 antibody purified product with a final concentration of 6 mg/mL was prepared. About 2 mg of ruthenium (manufactured by IGEN International, Inc.) was added to 1 mL of the antibody solution and stood at room temperature for 2 hours. Then, a mixture (2 mL) of 0.2 M glycine/PBS (pH 7.8) was added to block the surplus reactive sites. The ruthenium-labeled antibody solution was applied to ultrogel AcA44 gel chromatography and eluted with PBS containing 0.1% sodium azide to separate the labeled antibody which had been first eluted. The ruthenium labeled 12-1 monoclonal antibody thus prepared was stored at 4° C. until use as it was.

A chicken serum (manufactured by JRH Biosciences, Inc.) and the SM/PBS were mixed in equal amounts and used as a diluent for LN5 standard products and a diluent for labeled antibodies (hereinafter, abbreviated as Diluent). The MKN45 cell-derived purified LN5 obtained in Example 1 above was used as the standard products and diluted with the Diluent in LN5 concentrations of 1000, 500, 250, 125, 62.5, 31.25, and 15.625 ng/mL to prepare standard product solutions. Also, the each ruthenium-labeled antibody was diluted with the Diluent in 100-fold. Measurement of a biological sample was conducted using an automatic clinical analyzer (Picolumi 8220: manufactured by Sanko Junyaku Co, Ltd.). The standard product, a blood serum, and a blood plasma were each collected by 0.2 mL and added into dedicated reaction tubes, which were mounted to a dedicated reaction tube rack. The prepared antibody-bound beads and the labeled antibody were also contained in dedicated vessels, which were mounted to the automatic clinical analyzer. The process of automatic measurement was as follows. At first, 0.025 mL of the antibody-bound beads were added to the reaction tube and stirred intermittently for 9 minutes for carrying out the reaction with the first antibody. After removing the solution from the reaction tube by suction, washing with the washing solution was carried out twice. After washing, 0.2 mL of the ruthenium-labeled antibody solution was added and stirred intermittently for 9 minutes for carrying out the reaction with the second antibody. After removing the solution from the reaction tube by suction, washing with the washing solution was carried out twice. After the washing, 0.3 mL of emission electrolytic solution was added to measure the emission level.

Figure 7:
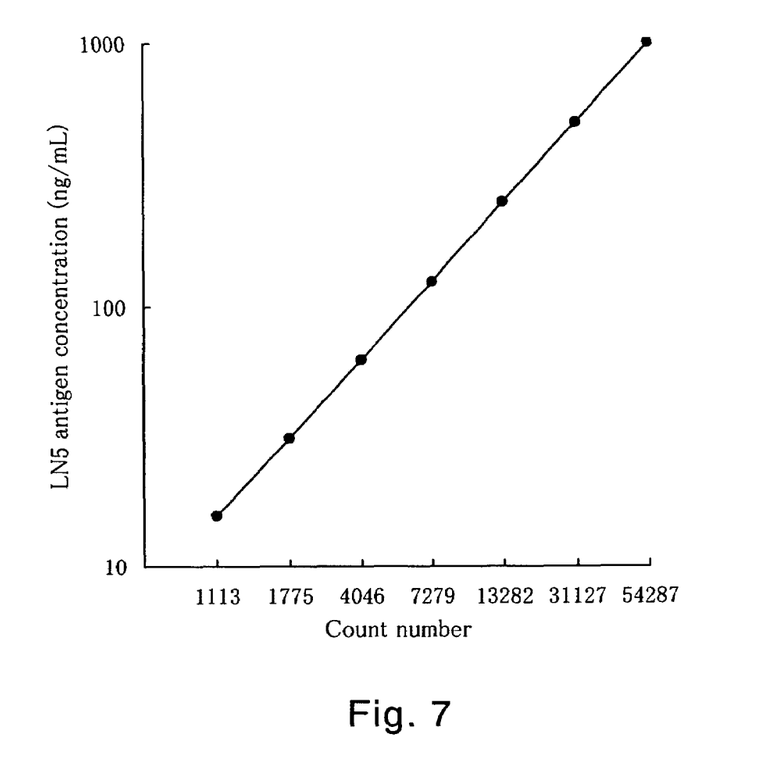
FIG. 7 shows a calibration curve in an electrochemiluminescence immunoassay using the KP2-LN5-8C2E 18-4 monoclonal antibody-immobilized beads and a ruthenium-labeled KP2-LN5-8C2E 12-1 monoclonal antibody.

A calibration curve was constructed based on the results for the standard antigens measured simultaneously to calculate the antigen level. The emission count number only for the Diluent was set as a blank value. Satisfactory measurements were possible in an antigen concentration range of 1000 to 15.625 ng/mL (FIG. 7).

Example 4

LN5 Antigen in Blood Serum from Nude Mouse Transplanted with Human Tumor (1) Orthotopic transplantation of human pancreatic tumor cell into nude mouse Three human pancreatic tumor cell lines (HPAC, MIA-paca-II, and KP-1) were each cultured in an RPMI-1640 medium supplemented with a 10% bovine fetal serum in a culture flask, and only cells were collected by a trypsin-EDTA solution treatment at a sufficiently grown stage. The cells were well washed and were orthotopically transplanted into pancreases of 8 week-aged nude mice (manufactured by Charles River Japan Inc.) under anesthesia. The mice transplanted with cells were bred in a clean room. At 2, 3, 4, and 5 weeks after the transplantation, three mice were randomly selected to sample blood from their hearts under ether anesthesia. The sampled whole blood was stood at 4° C. overnight and was then subjected to centrifugation to separate only sera. The separated sera were stored under freezing untill measurement. Furthermore, the mice were dissected after the blood sampling to extract portions of primary pancreatic tumor to be weighed.

(2) Measurement of LN5 Degraded Products in Mouse Serum

Figure 8:
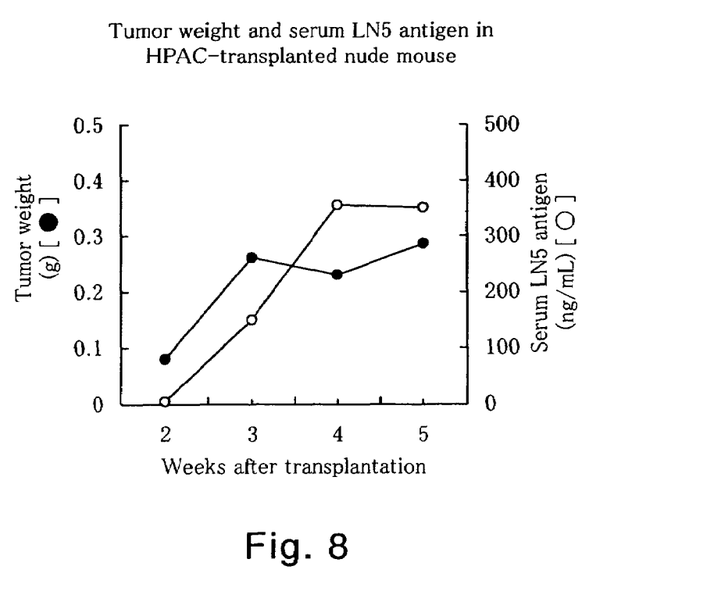
FIG. 8 shows changes in the weight of a primary tumor (●) and in the concentration of an LN5 antigen in a blood serum (○) of a nude mouse transplanted with the HPAC cell, at 2, 3, 4, and 5 weeks after the transplantation.

The LN5 antigens in the mice sera sampled in the previous item were measured in accordance with the detection method described in (3) in Example 3. The measurements revealed that the LN5 antigen derived from the transplanted cell was obviously released in the blood of the nude mouse transplanted with the HPAC cell. Those measurements also confirmed that the concentration of the LN5 antigens in blood increased in correlation with the enlargement of the primary tumor (FIG. 8).

Figure 9:
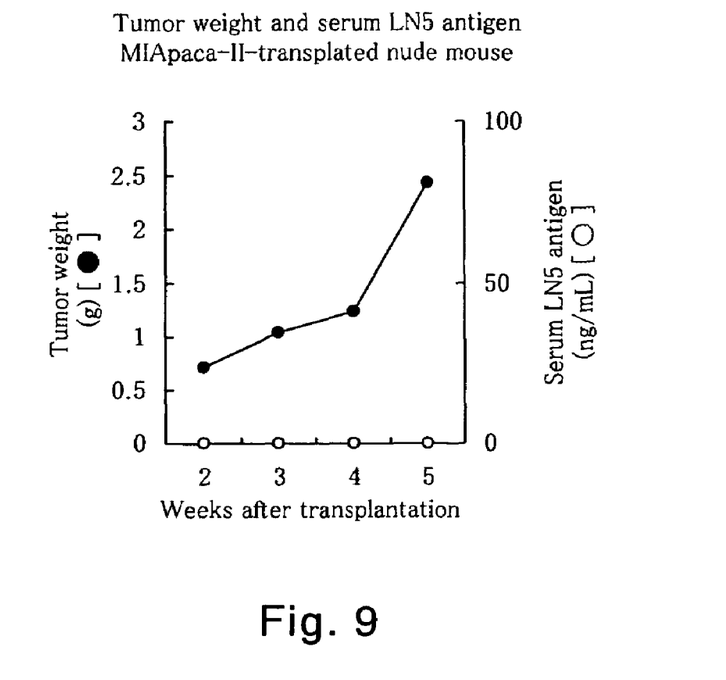
FIG. 9 shows a graph showing changes in the weight of a primary tumor (●) and in the concentration of an LN5 antigen in a blood serum (○) of a nude mouse transplanted with the MIApaca-II cell, at 2, 3, 4, and 5 weeks after the transplantation.

Further, the enlargement of the primary tumor was recognized in the nude mouse transplanted with the MIApaca-II cell having no LN5 antigen-production ability, while the increase in the concentration of the LN5 antigen in blood was not detected at all (FIG. 9).

Figure 10:
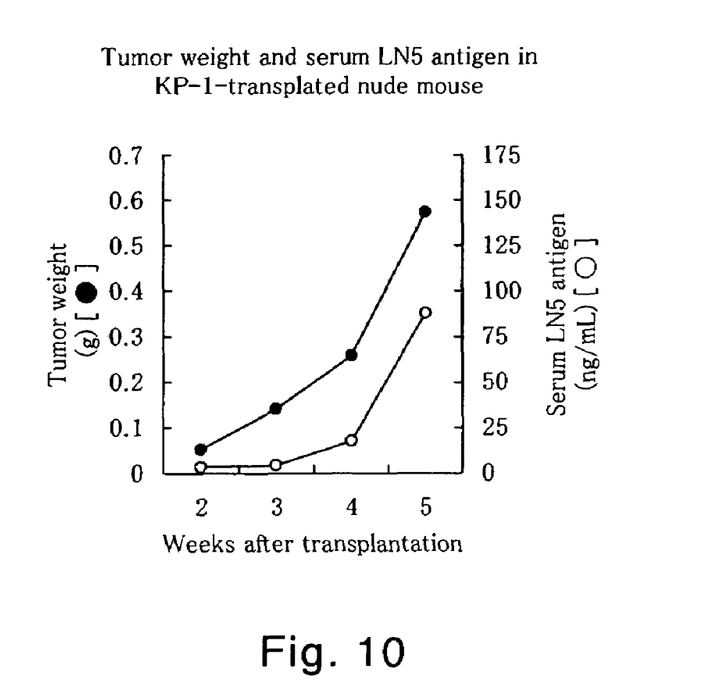
FIG. 10 shows changes in the weight of a primary tumor (●) and in the concentration of an LN5 antigen in a blood serum (○) of a nude mouse transplanted with the KP-1 cell, at 2, 3, 4, and 5 weeks after the transplantation.

Further, the experimental results in Example 2 have confirmed that the KP-1 cell has no ability to secrete the α3 chain and the β3 chain, and thus the cell has been considered to produce no LN5 antigen. However, in this examination, an increase in the LN5 antigen concentration correlating to the enlargement of the primary tumor was detected in the blood of the KP-1-transplanted nude mouse (FIG. 10). Therefore, it was shown that the KP-1 cell is a cell having a characteristic of producing a γ2 chain monomer of LN5, and it was thus shown that the LN5 antigen assay in accordance with the present assay method is useful for detecting a tumor of a γ2 chain monomer producing-type.

The above results have shown that the present assay method allows one to monitor the production of various kinds of LN5 antigens in a primary tumor.

Example 5

LN5 Antigen Concentration in Blood of Patients Suffering from ARDS (Acute Respiratory Distress Syndrome)

From the fact that a lung epithelial tissue is especially rich in LN5 among internal organs, the inventors hypothesized that the internal LN5 metabolism in a lung inflammatory disease increases. Thus, the LN5 antigen concentrations in blood plasma specimens sampled from healthy subjects and ARDS patients were determined in accordance with the assay method described in (3) in Example 3.

Figure 11:
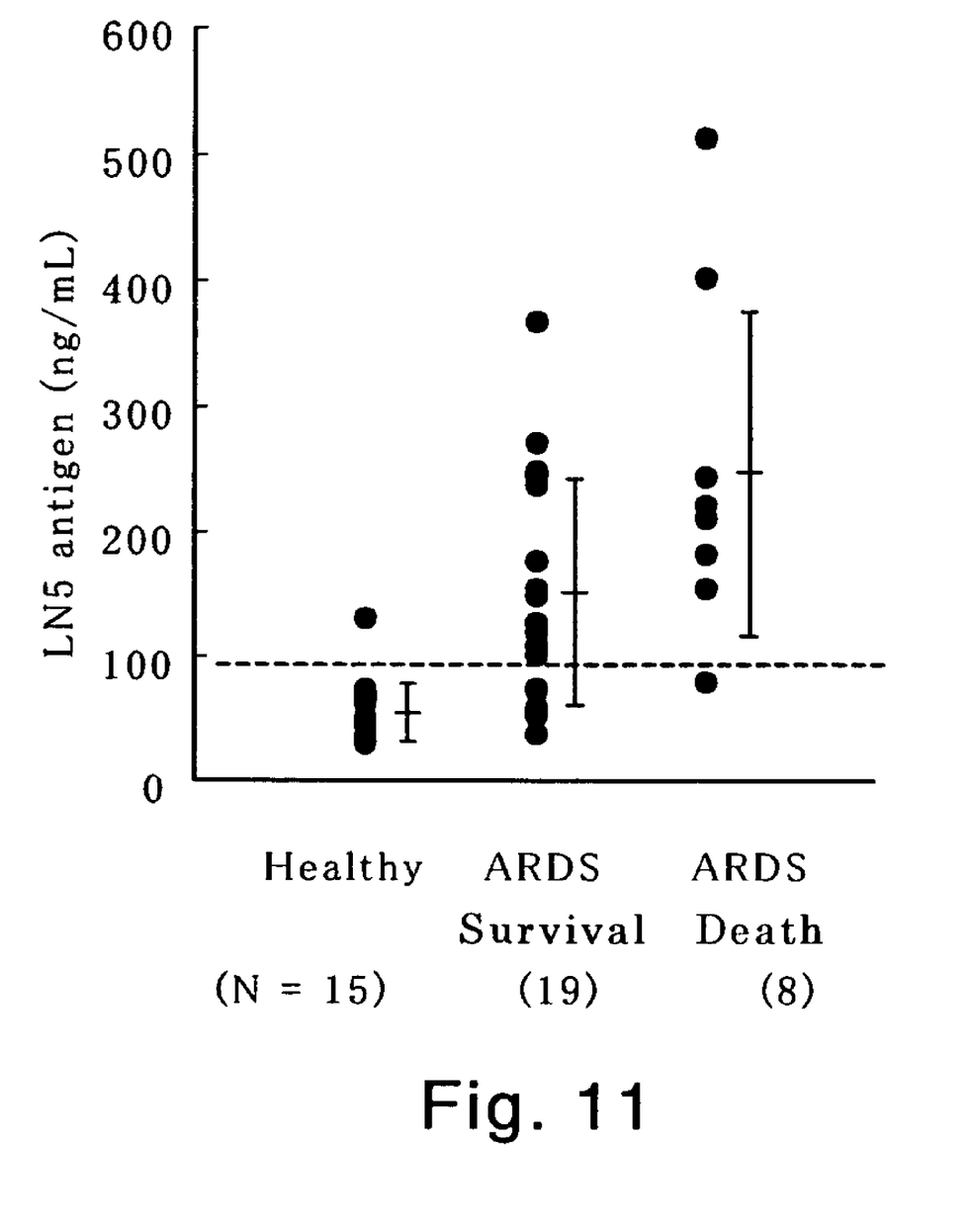
FIG. 11 is shows distribution, a mean value, and a standard deviation of an LN antigen concentration in a blood plasma for 27 ARDS patients and 15 healthy persons. The ARDS patients were classified into 19 survived cases (mild cases) and 8 non-survived cases (serious cases).

FIG. 11 shows the LN5 antigen concentrations in a blood plasma of 15 healthy persons, 19 survived ARDS patients, and 8 non-survived ARDS patients. The LN5 antigen concentrations in a blood plasma were 60.8 ng/mL, 158 ng/mL, and 250.9 ng/mL, respectively, showing that the concentrations in blood obviously increased in the group of ARDS patients. This finding confirmed that the LN5 antigen would be a novel marker in blood for diagnosis of ARDS and determination of the disease severity thereof.

Example 6

LN5 Antigen Concentrations in Blood of Patients Suffering from Various Digestive Organ Cancers The inventors hypothesized that LN5 is highly produced from epithelial malignant tumor cells. Thus, LN5 antigen concentrations in serum specimens sampled from 31 patients suffering from benign digestive diseases (8 diabetes patients and 25 chronic pancreatitis patients), 9 patients suffering from intraductal papillary-mucinous tumors, and 155 patients suffering from malignant digestive diseases (36 pancreatic carcinoma patients, 18 pancreatic carcinoma patients (with liver metastasis), 10 gastric cancer patients, 16 gallbladder and bile duct cancer patients, and 75 hepatic cancer patients) were determined in accordance with the assay method described in (3) in Example 3.

Figure 12:
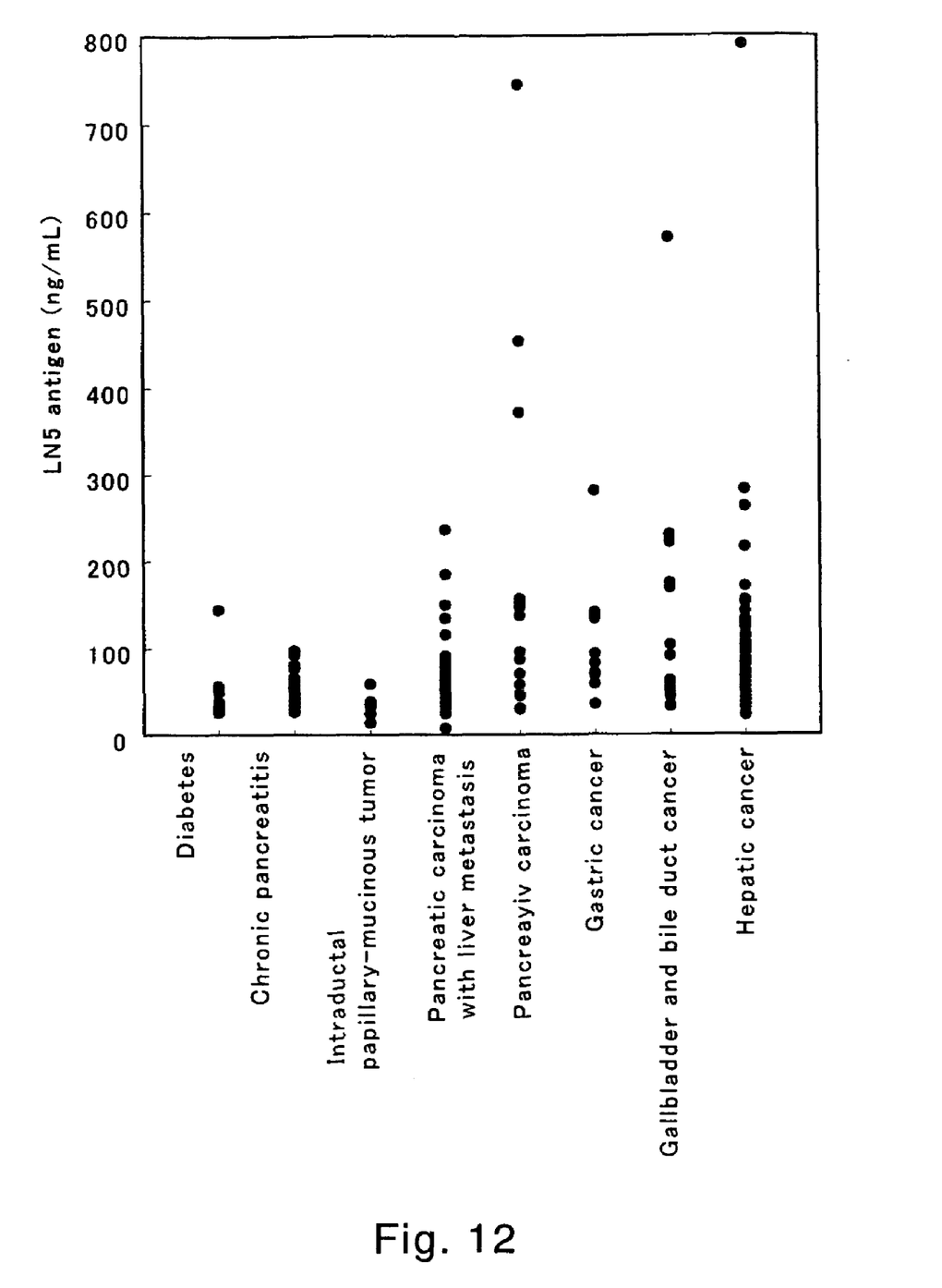
FIG. 12 shows distribution of the LN5 antigen concentration in a blood serum for 31 patients suffering from benign digestive disease, 9 patients suffering from intraductal papillary-mucinous tumor, and 155 patients suffering from malignant digestive disease.

FIG. 12 shows the LN5 antigen concentrations in blood sera of 8 diabetes patients, 25 chronic pancreatitis patients, 9 patients suffering from intraductal papillary-mucinous tumor diseases, 36 pancreatic carcinoma patients, 18 pancreatic carcinoma patients (with liver metastasis), 10 gastric cancer patients, 16 gallbladder and bile duct cancer patients, and 75 hepatic cancer patients. Mean values of the LN5 antigen concentrations in blood sera were 54.2 ng/mL, 50.6ng/mL, 35.0 ng/mL, 68.3 ng/mL, 165.9 ng/mL, 111.0 ng/mL, 136.0 ng/mL, and 121.9 ng/mL, respectively, showing that the concentrations in blood obviously increased in the group of the patients suffering from various digestive organ cancers. Additionally, there was detected a tendency of increasing the concentration in patients with liver metastasis. The detection confirmed that the LN5 antigen would be a novel marker in blood for determination of the malignancy of digestive organ cancers.

INDUSTRIAL APPLICABILITY

The present invention provides the reagent and the method of determining an LN5 antigen in a biological sample. Thus, it becomes possible to detect a tumor cell producing an LN5, to examine acute respiratory distress syndrome, and to determine the malignancy of a malignant tumor.

What is claimed is:

1. A method of detecting a laminin 5-producing tumor cell by determining an amount of a laminin 5 antigen in a blood specimen, comprising the steps of:
   bringing an antibody reactive to a laminin 5 γ2 chain N-terminal fragment into contact with the blood specimen;
   measuring a reaction of the antibody;
   determining an amount of the laminin 5 antigen based on a measurement result of the reaction; and
   detecting a laminin 5-producing tumor cell based on the determined amount of the laminin 5 antigen, wherein if the determined amount is high compared with healthy persons, the laminin 5-producing tumor cell is detected.

2. The method of claim 1, wherein the antibody is a monoclonal antibody produced from a cell deposited with an accession number selected from the group consisting of FERM BP-8136, FERM BP-8133, FERM BP-8134, and combinations thereof.

* * * * *